United States Patent
Luan et al.

(10) Patent No.: US 11,020,339 B2
(45) Date of Patent: Jun. 1, 2021

(54) COMPOSITION IN FORM OF AN EMULSION

(71) Applicant: L'OREAL, Paris (FR)

(72) Inventors: Tu Luan, Shanghai (CN); Yan Wang, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/708,254

(22) Filed: Dec. 9, 2019

(65) Prior Publication Data

US 2020/0113811 A1    Apr. 16, 2020

Related U.S. Application Data

(62) Division of application No. 15/026,369, filed as application No. PCT/CN2013/086305 on Oct. 31, 2013, now abandoned.

(51) Int. Cl.

| A61Q 1/02 | (2006.01) |
| A61Q 1/04 | (2006.01) |
| A61K 8/894 | (2006.01) |
| A61K 8/39 | (2006.01) |
| A61K 8/06 | (2006.01) |
| A61K 8/37 | (2006.01) |
| A61K 8/86 | (2006.01) |
| A61K 8/25 | (2006.01) |
| A61K 8/29 | (2006.01) |
| A61K 8/31 | (2006.01) |
| A61K 8/58 | (2006.01) |
| A61K 8/60 | (2006.01) |
| A61K 8/73 | (2006.01) |

(52) U.S. Cl.
CPC ............... *A61K 8/894* (2013.01); *A61K 8/06* (2013.01); *A61K 8/25* (2013.01); *A61K 8/29* (2013.01); *A61K 8/31* (2013.01); *A61K 8/375* (2013.01); *A61K 8/39* (2013.01); *A61K 8/585* (2013.01); *A61K 8/602* (2013.01); *A61K 8/732* (2013.01); *A61K 8/86* (2013.01); *A61Q 1/02* (2013.01); *A61Q 1/04* (2013.01); *A61K 2800/592* (2013.01); *A61K 2800/594* (2013.01); *A61K 2800/596* (2013.01)

(58) Field of Classification Search
None
See application file for complete search history.

(56) References Cited

U.S. PATENT DOCUMENTS

| 8,461,214 B2 | 6/2013 | Miyahara et al. |
| 8,529,918 B2 | 9/2013 | Gardel et al. |
| 2005/0008592 A1 | 1/2005 | Gardel et al. |
| 2006/0002425 A1 | 2/2006 | Gardel et al. |
| 2006/0024251 A1 | 2/2006 | Gardel et al. |
| 2006/0246026 A1 | 11/2006 | Bennett |
| 2006/0269499 A1 | 11/2006 | Gormley et al. |
| 2008/0226572 A1 | 9/2008 | Cassin |
| 2011/0104088 A1* | 5/2011 | Herzog ............... A61K 8/494 424/60 |
| 2011/0311598 A1 | 12/2011 | Amalric et al. |

FOREIGN PATENT DOCUMENTS

| CN | 1447676 A | 10/2003 |
| CN | 1471903 A | 2/2004 |
| CN | 101873846 A | 10/2010 |
| JP | 2006-213710 A | 8/2006 |
| KR | 10-1129410 B1 | 3/2012 |
| WO | WO 96/36309 | 11/1996 |
| WO | WO 03/000223 A1 | 1/2003 |
| WO | WO 2004/103322 A1 | 12/2004 |
| WO | WO 2006/013415 A1 | 2/2006 |

OTHER PUBLICATIONS

Indian Examination Report dated Apr. 3, 2019, in Patent Application No. 201647012585, 5 pages.
International Search Report dated Jul. 25, 2014, in PCT/CN2013/086305 filed Oct. 31, 2013.
Written Opinion of the International Searching Authority dated Jul. 25, 2014, in PCT/CN2013/086305 filed Oct. 31, 2013.
Extended Search Report dated Mar. 27, 2017 in European Patent Application No. 13896366.5.
Japanese Office Action dated Jul. 31, 2017 in Patent Application No. 2016-523307 (with English Translation).
Office Action dated Aug. 22, 2017 in Korean Patent Application No. 10-2016-7008419 (with English language translation).
Combined Office Action and Search Report dated Sep. 3, 2018 in Chinese Patent Application No. 201380080313.6, 12 pages (with English translation of categories of cited documents).

* cited by examiner

*Primary Examiner* — Jyothsna A Venkat
(74) *Attorney, Agent, or Firm* — Oblon, McClelland, Maier & Neustadt, L.L.P.

(57) ABSTRACT

The present invention is a composition in form of an emulsion, comprising at least one fatty phase, and at least one aqueous phase, and:

a) at least one first surfactant chosen from $C_8$-$C_{22}$ alkyl dimethicone copolyols;

b) at least one second surfactant chosen from dimethicone copolyols, which is different from the first surfactant a);

c) at least one third surfactant which is different from the first or the second surfactant a) or b), having a HLB value of greater than or equal to 8; and d) at least one hydrophilic pigment.

1 Claim, No Drawings

COMPOSITION IN FORM OF AN EMULSION

CROSS REFERENCE TO RELATED APPLICATIONS

This application is a divisional application of prior U.S. application Ser. No. 15/026,369, filed Mar. 31, 2016, the disclosure of which is incorporated herein by reference in its entirety. U.S. application Ser. No. 15/026,369 is the national stage of PCT/CN2013/086305, filed Oct. 31, 2013, the disclosure of which is incorporated herein by reference in its entirety.

TECHNICAL FIELD

The present invention relates to a composition, especially cosmetic composition for caring for/making up the keratin materials, especially the skin and the lips, and more particularly a cosmetic composition of emulsion type, exhibiting optimized water washability effect, and meanwhile maintaining good make up effect.

BACKGROUND ART

Cosmetic compositions for caring for/making up keratin materials, especially the skin and the lips, more especially the skin, also known as foundations, concealers, or tinted creams, are commonly used to give an aesthetic color to the skin, for example, to the face, in order to conceal skin imperfections such as redness and spots.

For centuries, consumers around the world, especially in Asia, are in search of novel cosmetic products for improving the appearance of keratin materials and especially the skin, in particular the surface appearance (visible and/or tactile unevenness) and/or the skin complexion, an external sign of a healthy glow, health and youth.

These goals can be achieved by applying to the skin the conventional foundations.

US2005/0008592 discloses a foundation in the formula of a water-in-oil emulsion comprising a fatty phase, an aqueous phase, at least one surfactant chosen from $C_8$-$C_{22}$ alkyl dimethicone copolyols, at least one other surfactant chosen from dimethicone copolyols and a mixture of volatile oils in a large amount (more than 6%).

US2005/0002890 also discloses a fluid cosmetic composition in the form of a water-in-oil emulsion comprising a liquid fatty phase, an aqueous phase, a dimethicone copolyol and a $C_5$-$C_{22}$ alkyldimethicone copolyol, characterized in that it comprises solid particles of polymethyl methacrylate and in that the liquid fatty phase comprises volatile hydrocarbon-based oil, the said composition being free of cyclotetrasiloxane.

However, the conventional products as such raise concerns of the consumers in the following aspects: firstly, pigments containing in the foundation may cause clogging issue to the skin pores; secondly, removing of the foundation is time consuming and a cause of skin keratinization; thirdly, residues remain on skin even after using makeup removal.

Thus there exists a need for a novel composition to solve the issues aforementioned.

Conventional oil-in-water type foundation/tinted creams are developed to solve the water washability issue. However this type of compositions can only be partly removed by water, therefore exhibits poor water washability. Besides, the compositions as such lack of long-lasting make up effect due to its hydrophilic property.

Therefore there remains the need to find stable care and/or makeup products, which exhibits an optimized water washability effect, and at the same time possesses good make up effect, for example homogeneous and long-lasting make up effect.

DISCLOSURE OF INVENTION

Such a composition can be obtained using at least one first surfactant chosen from alkyl dimethicone copolyols, at least one second surfactant chosen from dimethicone copolyols, which is different from the first surfactant, at least one third surfactant which is different from the first or the second surfactant, having a HLB value of greater than or equal to 8, and at least one hydrophilic pigment.

Consequently, according to a first aspect, the subject of the present invention is a composition in form of an emulsion, comprising at least one fatty phase, and at least one aqueous phase, and:
  a) at least one first surfactant chosen from $C_8$-$C_{22}$ alkyl dimethicone copolyols;
  b) at least one second surfactant chosen from dimethicone copolyols, which is different from the first surfactant a);
  c) at least one third surfactant which is different from the first or the second surfactant a) or b), having a HLB value of greater than or equal to 8; and
  d) at least one hydrophilic pigment.

According to a preferred embodiment, the composition of the present invention is in form of a multiple emulsion, such as water-in-oil-in-water emulsion, or oil-in-water-in-oil emulsion, preferably an oil-in-water-in-oil emulsion.

In a preferred embodiment, the present invention comprises at least one filler, organic or mineral, chosen from modified or unmodified starch, preferably modified starch, such as acetylated oxidized starch.

According to a preferred embodiment, the present invention comprises at least one thickener, polymeric or mineral, preferably chosen from hydrophilic thickeners, lipophilic thickeners, or a mixture thereof. More preferably the thickener is chosen from polysaccharide biopolymers, lipophilic clays, hydrophobic silicas, or a mixture thereof, more preferably the thickener is chosen xanthan gum, disteardimonium hectorite, silica silylate, or a mixture thereof.

In another aspect, the present invention is also directed towards a process for caring for/making up the skin, in particular the face, characterized in that it comprises the application to the skin of at least one composition in accordance with the invention.

The current invention as described above is stable over time at room temperature (25° C.), for example, after storage for 2 months, and further, for example, for 4 months.

The present invention provides good make up effect to the skin, such as homogeneous make up effect on the skin, and long lasting make up effect on the skin.

More importantly, the present invention possesses an optimized water washability property.

By "water washability" it intends to mean the washable ability of the present composition when using water for rinsing off from the skin.

DETAILED DESCRIPTION OF THE INVENTION

According to the present invention, the composition in form of an emulsion comprising at least one fatty phase, at least one aqueous phase, and:

a) at least one first surfactant chosen from $C_8$-$C_{22}$ alkyl dimethicone copolyols;
b) at least one second surfactant chosen from dimethicone copolyols, which is different from the first surfactant a);
c) at least one third surfactant which is different from the first or the second surfactant a) or b), having a HLB value of greater than or equal to 8; and
d) at least one hydrophilic pigment.

Fatty Phase

The composition according to the present invention comprises at least one fatty phase containing at least one oil.

Preferably, according to an embodiment, the composition of the present invention comprises at least two fatty phases.

The term "oil" means any fatty substance that is in liquid form at room temperature (20-25° C.) and at atmospheric pressure (760 mmHg).

The fatty phase(s) that is suitable for preparing the cosmetic compositions according to the invention may comprise hydrocarbon-based oils, silicone oils, fluoro oils or non-fluoro oils, or mixtures thereof.

The oils may be volatile or non-volatile.

According to a preferred embodiment, when present, the ratio between volatile oil and non-volatile oil is greater than or equal to 1:3, more preferably greater than or equal to 1:1. They may be of animal, plant, mineral or synthetic origin.

The term "non-volatile oil" means oil that remains on the keratin materials, especially the skin and the lips at room temperature (20-25° C.) and atmospheric pressure (760 mmHg). More specifically, non-volatile oil has an evaporation rate strictly less than 0.01 mg/cm²/min.

To measure this evaporation rate, 15 g of oil or of oil mixture to be tested are placed in a crystallizing dish 7 cm in diameter, which is placed on a balance in a large chamber of about 0.3 m³ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said oil mixture, the blades being directed towards the crystallizing dish, 20 cm away from the bottom of the crystallizing dish. The mass of said oil or oil mixture remaining in the crystallizing dish is measured at regular intervals. The evaporation rates are expressed in mg of oil evaporated per unit of area (cm²) and per unit of time (minute).

The term "volatile oil" means any non-aqueous medium that is capable of evaporating on contact with the keratin materials, especially the skin and the lips in less than one hour, at room temperature (20-25° C.) and atmospheric pressure (760 mmHg). The volatile oil is a cosmetic volatile oil, which is liquid at room temperature. More specifically, a volatile oil has an evaporation rate of between 0.01 and 200 mg/cm²/min, limits included.

For the purposes of the present invention, the term "silicone oil" means oil comprising at least one silicon atom, and especially at least one Si—O group.

The term "fluoro oil" means oil comprising at least one fluorine atom.

The term "hydrocarbon-based oil" means oil mainly containing hydrogen and carbon atoms.

As hydrocarbon-based oils, mention may be made of
hydrocarbon-based oils of animal origin, hydrocarbon-based oils of plant origin,
linear or branched hydrocarbons of mineral or synthetic origin,
synthetic ethers containing from 10 to 40 carbon atoms;
synthetic esters,
fatty alcohols that are liquid at room temperature, with a branched and/or unsaturated carbon-based chain containing from 12 to 26 carbon atoms,
$C_{12}$-$C_{22}$ higher fatty acids, and
mixtures thereof.

Mentions maybe made of the hydrocarbon-based oils such as liquid paraffins and derivatives thereof, petroleum jelly, polydecenes, polybutenes, hydrogenated polyisobutene such as Parleam, and squalane, for example Squalane which is available under the trademark Pripure 3759-LQ-(GD) sold by Croda.

The oils may optionally comprise oxygen, nitrogen, sulfur and/or phosphorus atoms, for example in the form of hydroxyl or acid radicals.

According to a preferred embodiment, the composition of the present invention further comprises silicone oils.

As silicone oils, mention may be made of:
linear or cyclic volatiles oils, especially those with a viscosity of less than or equal to 8 centistokes (cSt) ($8 \times 10^{-6}$ m²/s), and especially containing from 2 to 10 silicon atoms and in particular from 2 to 7 silicon atoms, these silicones optionally comprising alkyl or alkoxy groups containing from 1 to 10 carbon atoms;
of linear or cyclic non-volatile polydimethylsiloxanes (PDMS); polydimethylsiloxanes comprising alkyl, alkoxy or phenyl groups, which are pendant or at the end of a silicone chain, these groups containing from 2 to 24 carbon atoms;
phenyl silicones, for instance phenyl trimethicones, phenyl dimethicones, phenyl trimethylsiloxy diphenyl siloxanes, diphenyl dimethicones, diphenyl methyldiphenyl trisiloxanes and 2-phenylethyl trimethylsiloxy silicates,
and mixtures thereof In a particular embodiment, mention may be made of cyclohexasiloxane which is available under the trademark, for example, KF-996 sold by the company Shin Etsu, or Xiameter® PMX-0246 sold by the company Dow Corning, or dimethicones which is available under the trademark Xiameter® PMX-200 silicone fluid 5 cs, Xiameter® PMX-200 silicone fluid 350 cs, or Xiameter® PMX-200 silicone fluid 10 cs sold by the company Dow Corning.

Preferably, the composition may comprise a fatty phase presenting in the composition in a content ranging from 1% to 50%, preferably from 2% to 40%, and more preferably from 5% to 35% by weight relative to the total weight of the composition.

Aqueous Phase

The composition according to the invention comprises at least one aqueous phase.

The aqueous phase comprises water.

The aqueous phase may also comprise water-miscible organic solvents (at room temperature of 20-25° C.), for instance monoalcohols containing from 2 to 6 carbon atoms, such as ethanol or isopropanol; polyols especially containing from 2 to 20 carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$)alkyl ethers, mono-, di- or triethylene glycol ($C_1$-$C_4$)alkyl ethers, and mixtures thereof.

The aqueous phase may also comprise stabilizers, for example sodium chloride, magnesium dichloride or magnesium sulfate.

In particular, a composition of the invention may comprise an aqueous phase in a content ranging from 1% to 90% by weight, especially from 5% to 80% and more particularly from 10% to 75% by weight relative to the total weight of the composition.

$C_8$-$C_{22}$ Alkyl Dimethicone Copolyols

The $C_8$-$C_{22}$ alkyl dimethicone copolyols present in the composition according to the invention is an oxypropylenated and/or oxyethylenated polymethyl ($C_8$-$C_{22}$)alkyl dimethyl methyl siloxane.

The $C_8$-$C_{22}$ alkyl dimethicone copolyol is advantageously a compound of the following formula (I):

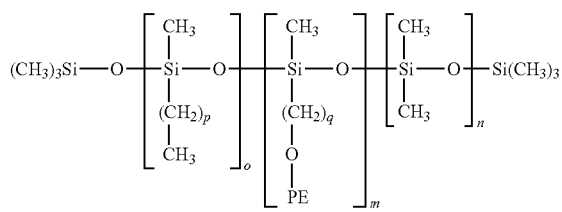

in which:

PE represents $(-C_2H_4O)_x-(C_3H_6O)_y-R$, R being chosen from a hydrogen atom and an alkyl radical of 1 to 4 carbon atoms, x ranging from 0 to 100 and y ranging from 0 to 80, x and y not being simultaneously 0, m ranges from 1 to 40, n ranges from 10 to 200, o ranges from 1 to 100, p ranges from 7 to 21, q ranges from 0 to 4, and preferably:

R=H, m=1 to 10, n=10 to 100, o=1 to 30, p=15, q=3.

As $C_8$-$C_{22}$ alkyl dimethicone copolyol, there may be mentioned cetyl dimethicone copolyols, for example, copolyols of cetyl dimethicones and alkoxylated derivative of dimethicones, more preferably for example cetyl PEG/PPG-10/1 dimethicone, such as the product marketed under the name Abil® EM-90 by the company Goldschmidt.

The $C_8$-$C_{22}$ alkyl dimethicone copolyol may be present in the composition according to the invention in an amount ranging from 0.1% to 20% by weight, relative to the total weight of the emulsion, in particular ranging from 0.5% to 10% by weight, even better ranging from 1% to 5% by weight, relative to the total weight of the composition.

Dimethicone Copolyols

The dimethicone copolyols, which is different from $C_8$-$C_{22}$ alkyl dimethicone copolyols mentioned above, present in the composition according to the invention is an oxypropylenated and/or oxyethylenated polydimethylmethylsiloxane.

It is possible to use, as dimethicone copolyol, those corresponding to the following formula (II):

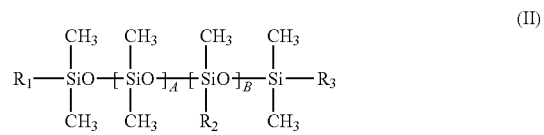

in which:

$R_1$, $R_2$, $R_3$, independently of each other, represent a $C_1$-$C_6$ alkyl radical or a radical $-(CH_2)_x-(OCH_2CH_2)_y-(OCH_2CH_2)_z-OR_4$, at least one radical $R_1$, $R_2$ or $R_3$ not being an alkyl radical; $R_4$ being hydrogen, a $C_1$-$C_3$ alkyl radical or a $C_2$-$C_4$ acyl radical;

A is an integer ranging from 0 to 200;

B is an integer ranging from 0 to 50; provided that A and B are not equal to zero at the same time;

x is an integer ranging from 1 to 6;

y is an integer ranging from 1 to 30;

z is an integer ranging from 0 to 5.

According to a preferred embodiment of the invention, in the compound of formula (II), $R_1$=$R_3$=methyl radical, x is an integer ranging from 2 to 6 and y is an integer ranging from 4 to 30. $R_4$ is in particular hydrogen.

There may be mentioned, by way of example of compounds of formula (II), the compounds of formula (III):

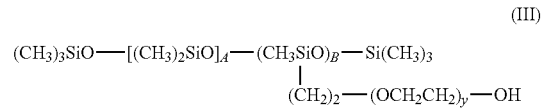

in which A is an integer ranging from 20 to 105, B is an integer ranging from 2 to 10 and y is an integer ranging from 10 to 20.

There may also be mentioned, by way of example of silicone compounds of formula (II), the compounds of formula (IV):

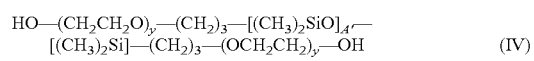

in which A' and y are integers ranging from 10 to 20.

It is possible to use, as dimethicone copolyol, those sold under the names DC® 5329, DC® 7439-146, DC® 2-5695, Q4-3667 by the company Dow Corning; KF-6013, KF-6015, KF-6016, KF-6017 by the company Shin-Etsu.

The compounds DC® 5329, DC® 7439-146, DC® 2-5695 are compounds of formula (III) where respectively A is 22, B is 2 and y is 12; A is 103, B is 10 and y is 12; A is 27, B is 3 and y is 12.

Advantageously, mentions maybe made of the dimethicone copolyol PEG-10 dimethicone under the trademark KF-6017 that is sold by the company Shin-Etsu.

The dimethicone copolyol may be present in the emulsion according to the invention in an amount ranging from 0.1% to 20% by weight, relative to the total weight of the composition, and preferably ranging from 0.5% to 10% by weight, and preferably ranging from 0.8% to 5% by weight, even more preferably 3% by weight, relative to the total weight of the composition.

Third Surfactant

The composition of the present invention comprises at least one third surfactant. The third surfactant is different from the first or second surfactant aforementioned. The third surfactant has a HLB value of greater than or equal to 8, according to Griffin's method, at the temperature of 25° C.

The HLB value according to GRIFFIN is defined in J. Ploughshare. Cosm. Chem. 1954 (volume 5), pages 249-256.

Preferably, the third surfactant has a HLB value between 8 and 20 according to Griffin's method, at the temperature of 25° C., more preferably between 10 and 15 according to Griffin's method, at the temperature of 25° C.

Preferably, the third surfactant is chosen from non-ionic surfactants, anionic surfactants, amphoteric or zwitterionic surfactant, or a mixture thereof.

Non-ionic surfactants that are suitable to the present composition may be chosen from:

- polyoxyethylenated sorbitol fatty esters such as the product sold under the name TWEEN 20 by ICI;
- polyoxyethylenated fatty alcohols such as the product sold under the name REMCOPAL 21912 AL by Gerland;
- polyoxyethylenated alkylphenols such as the product sold under the name TRITON X 100 by Röhm-Haas; and
- condensates of ethylene oxide and of propylene oxide such as those sold under the names SYNPERONIC PE by ICI and in particular those referenced L 31, L 64, F 38, F 88, L 92, P 103, F 108 and F 127;
- esters of fatty acids and glycerol or polyglycerol, preferably esters of $C_6$-$C_{30}$, more preferably $C_8$-$C_{16}$, fatty acids, saturated or unsaturated, and glycerol or polyglycerol. Mentions may be made of for example glyceryl stearate, glyceryl isostearate, polyglyceryl-3 diisostearate, PEG-100 stearate, glyceryl caprylate, polyglyceryl 1-4 caprate, or a mixture thereof. Such products are available on the market, for example, a mixture of glyceryl stearate and PEG-100 stearate is available under the tradename Simulsol™ 165 sold by the company Seppic, or such as the product polyglyceryl 1-4 caprate sold under the tradename Tegosoft® PC 41 by the company Evonik Goldshmidt.
- ethers of polyethylene glycol and/or of polypropylene glycol, and of glycerol such as glycereth-26 and PPG-24 glycereth-24;
- esters derived from the reaction a) of fatty acids and b) polyethylene glycol and/or polypropylene glycol glycerol ethers such as, for example, glycereth-7, or glycereth-25 PCA isostearate;
- esters of sucrose and of fatty acids comprising from 12 to 30 carbon atoms, in particular 14 to 20 carbon atoms, said esters possibly comprising from 2 to 5 fatty chains, such as for example sucrose distearate, sucrose tristearate and sucrose palmitate;
- alkylpolyglucosides, preferably those that contain an alkyl group comprising from 6 to 30 carbon atoms and preferably from 8 to 16 carbon atoms, and that contain a hydrophilic group (glucoside) preferably comprising 1.2 to 3 sugar units. Mention may be made, for example, of decyl glucoside (Alkyl-$C_9$/$C_{11}$-polyglucoside (1.4)) such as the product sold under the name Plantacare® 2000 UP by Cogins (BASF), products sold under the name MYDOL 10® by Kao Chemicals, the product sold under the name PLANTAREN® 2000 UP by Cognis, and the product sold under the name ORAMIX® NS 10 by Seppic; caprylyl/capryl glucoside such as the product sold under the name ORAMIX® CG 110 by Seppic; laurylglucoside such as the products sold under the names PLANTAREN® 1200 N and PLANTACARE® 1200 by Cognis; and cocoglucoside such as the product sold under the name PLANTACARE® 818/UP by Cognis, cetostearylglucoside optionally as a mixture with cetostearyl alcohol sold, for example, under the name MONTANOV 68 by Seppic under the name TEGO® CARE CG90 by Goldschmidt and under the name EMULGADE KE3302 by Henkel; arachidylglucoside, for example in the form of the mixture of arachidyl and behenyl alcohols and of arachidylglucoside sold under the name MONTANOV 202 by Seppic; cocoylethylglucoside, for example in the form of the (35/65) mixture with cetyl and stearyl alcohols, sold under the name MONTANOV 82 by Seppic and mixtures thereof.

Mention may in particular be made, among anionic surfactants, of:

- alkyl sulphates, alkyl ether sulphates and their salts, in particular their sodium salts, such as the Sodium Laureth Sulphate/Magnesium Laureth Sulphate/Sodium Laureth-8 Sulphate/Magnesium Laureth-8 Sulphate mixture sold under the name TEXAPON ASV by Henkel; sodium lauryl ether sulphate ($C_{12-14}$ 70/30) (2.2 EO), sold under the names SIPON AOS 225 or TEXAPON® N702 PASTE by Henkel; ammonium lauryl ether sulphate ($C_{12-14}$ 70/30) (3 EO) sold under the name SIPON LEA 370 by Henkel; ammonium alkyl ($C_{12-C14}$) ether (9 EO) sulphate, sold under the name RHODAPEX® AB/20 by Rhodia Chimie;
- alkyl sulphoacetates, such as that sold under the name LATHANOL® LAL by Stepan;
- alkyl sulphosuccinates, for example the oxyethylenated (3 EO) lauryl alcohol ($C_{12}$/$C_{14}$ 70/30) monosulphosuccinate sold under the names SETACIN 103 SPECIAL or REWOPOL SB-FA 30 K 4 by Witco, the disodium salt of a hemisulphosuccinate of $C_{12}$-$C_{14}$ alcohols sold under the name SETACIN F SPECIAL PASTE by Zschimmer Schwarz, the oxyethylenated (2 EO) disodium oleamidosulphosuccinate sold under the name STANDAPOL SH 135 by Henkel, the oxyethylenated (5 EO) lauramide monosulphosuccinate sold under the name LEBON A-5000 by Sanyo, the disodium salt of oxyethylenated (10 EO) lauryl citrate monosulphosuccinate sold under the name REWOPOL® SB CS 50 by Witco or the disodium salt of ricinoleic acid monoethanolamide monosulphosuccinate sold under the name REWODERM® S 1333 by Witco;
- polypeptides which are obtained, for example, by condensation of a fatty chain with cereal amino acids and in particular wheat and oat amino acids, such as, for example, the potassium salt of lauroyl hydrolysed wheat protein sold under the name AMINOFOAM™ W OR by Croda, the triethanolamine salt of cocoyl hydrolysed soya protein sold under the name MAYTEIN SY by Maybrook, the sodium salt of lauroyl oat amino acids sold under the name PROTEOL™ OAT by Seppic, the hydrolysate of collagen grafted to coconut fatty acid sold under the name GELIDERM 3000 by Deutsche Gelatine or the soya proteins acylated with hydrogenated coconut acids sold under the name PROTEOL VS 22 by Seppic;
- amino acid derivatives, for example among sarcosinates and in particular acylsarcosinates, such as sodium lauroyl sarcosinate, sold under the name SARKOSYL NL 97 by Ciba or sold under the name ORAMIX™ L 30 by Seppic, sodium myristoyl sarcosinate, sold under the name NIKKOL SARCOSINATE MN by Nikkol, or sodium palmitoyl sarcosinate, sold under the name NIKKOL SARCOSINATE PN by Nikkol; alaninates, such as sodium N-lauroyl-N-methylamidopropionate, sold under the name SODIUM NIKKOL ALANINATE LN 30 by Nikkol or sold under the name ALANONE ALE by Kawaken, and triethanolamine methylalanine, sold under the name ALANONE ALTA by Kawaken; N-acylglutamates, such as triethanolamine monococoyl glutamate, sold under the name ACYLGLUTAMATE CT-12 by Ajinomoto, and triethanolamine lauroyl glutamate, sold under the name ACYLGLUTAMATE LT-12 by Ajinomoto; aspartates, such as the mixture of triethanolamine N-lauroyl aspartate and of triethanolamine N-myristoyl aspartate sold under the name ASPARACK LM-TS2 by Mitsubishi; or glycine derivatives, such as sodium N-cocoyl glycinate and potassium N-cocoyl glycinate, for example the products sold under the names AMILITE GCS-12 and AMILITE GCK-12 by Ajinomoto;

sulphonates, for example α-olefin sulphonates, such as the sodium α-olefin ($C_{14-16}$) sulphonate sold under the name BIO-TERGE® AS-40 by Stepan, sold under the names WITCONATE AOS PROTÉGÉ and SULFRAMINE AOS PH 12 by Witco or sold under the name BIO-TERGE® AS-40 CG by Stepan or the sodium secondary olefin sulphonate sold under the name HOSTAPUR® SAS 30 by Clariant; or linear alkylarylsulphonates, such as the sodium xylenesulphonate sold under the names MANROSOL SXS30, MANROSOL SXS40 or MANROSOL SXS93 by Manro;

isethionates, in particular acyl isethionates, such as sodium cocoyl isethionate, for example the product sold under the name JORDAPON CI P by Jordan.

Mention may in particular be made, among amphoteric or zwitterionic surfactants, of:

alkylamido alkylamine derivatives, such as N-disodium N-cocoyl-N-carboxymethoxyethyl-N-(carboxymethyl)ethylenediamine (CTFA name: Disodium cocoamphodiacetate), sold as a saline aqueous solution under the name MIRANOL C2M CONC NP by Rhodia Chimie; N-sodium N-cocoyl-N-hydroxyethyl-N-(carboxymethyl)ethylene-diamine (CTFA name: sodium cocoamphoacetate) and the mixture of coconut acid ethanolamides (CTFA name: Cocamide DEA);

betaines, such as, for example, coca betaine, such as the product sold under the name DEHYTON® AB-30 by Henkel, lauryl betaine, such as the product sold under the name GENAGEN® KB by Clariant, oxyethylenated (10 EO) lauryl betaine, such as the product sold under the name LAURYL ETHER (10 EO) BETAINE by Shin Nihon Rica, or oxyethylenated (10 EO) stearyl betaine, such as the product sold under the name STEARYL ETHER (10 EO) BETAINE by Shin Nihon Rica;

alkyl amidopropyl betaines and their derivatives, such as, for example, cocamidopropyl betaine, sold under the name LEBON 2000 HG by Sanyo or sold under the name EMPIGEN® BB by Albright & Wilson, lauramidopropyl betaine, sold under the name REWOTERIC AMB12P® by Witco, such as cocamidopropyl betaine, for example the products sold under the names TEGO BETAINE by Goldschmidt;

imidazoline derivatives, such as the product sold under the name CHIMEXANE HD by Chimex; and their mixtures.

Preferably, the third surfactant is chosen from non-ionic surfactants.

More preferably, the third surfactant is chosen from esters of fatty acides and glycerol or polyglycerol, alkylpholyglucosides, or a mixture thereof.

More preferably, the third surfactant is chosen from esters of fatty acides and glycerol or polyglycerol of $C_6$-$C_{30}$, more preferably $C_6$-$C_{16}$, fatty acids, saturated or unsaturated, and glycerol or polyglycerol, alkylpolyglucosides containing an alkyl group comprising from 6 to 30 carbon atoms, preferably from 8 to 16 carbon atoms, and containing a hydrophilic group (glycoside) preferably comprising 1.2 to 3 sugar units, or a mixture thereof.

According to a preferred embodiment, the third surfactant of the present invention is chosen from glyceryl stearate, PEG-100 stearate, polyglyceryl-4 caprate, decyl glucoside, or a mixture thereof.

Preferably, the at least one third surfactant is present in the composition of the present invention from 0.1% to 20% by weight, preferably from 0.5% to 10% by weight, more preferably from 1% to 5% by weight, relative to the total weight of the composition.

Hydrophilic Pigments

The composition according to the present invention comprises at least one hydrophilic pigment, surface treated or untreated.

The hydrophilic pigments can be hydrophilic pigments in an untreated state, or can be pigments which have been surface-treated for hydrophilization, or a mixture thereof.

According to a preferred embodiment, the composition of the present invention comprises at least one treated hydrophilic pigment.

The hydrophilic pigments may be any type which has conventionally been used or is usable in the fields of cosmetics, examples of which include inorganic pigments, organic pigments, pearlescent pigments.

The term "pigments" should be understood as meaning white or coloured, mineral or organic particles that are insoluble in an aqueous solution, which are intended to colour and/or opacify the resulting film.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof. According to one preferred mode, titanium oxides and dioxides and iron oxides (especially yellow, black or red iron oxide), and mixtures thereof, will be used.

Among the organic pigments that may be used in the invention, mention may be made of carbon black, pigments of D & C type, lakes based on cochineal carmine or on barium, strontium, calcium or aluminium, or alternatively the diketopyrrolopyrroles (DPP) described in documents EP-A-0 542669, EP-A-0 787730, EP-A-0 787731 and WO-A-96/08537.

Advantageously, the pigments in accordance with the invention are iron oxides and/or titanium dioxides.

The term 'pearlescent pigments' or "nacres" should be understood as meaning coloured particles of any form, which may or may not be iridescent, especially produced by certain mollusks in their shell, or alternatively synthesized, and which have a colour effect via optical interference.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

The nacres may more particularly have a yellow, pink, red, bronze, orange, brown, gold and/or coppery colour or glint.

As illustrations of nacres that may be used in the context of the present invention, mention may be made of gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the names Bronze fine (17384) (Colorona) and Bronze (17353) (Colorona) and by the company Engelhard under the name Super bronze (Cloisonne); the orange nacres sold especially by the company Engelhard under the names Orange 363C (Cloisonne) and Orange MCR 101 (Cosmica) and by the company Merck under the names Passion orange (Colorona) and Matte orange (17449) (Microna); the brown-tinted nacres sold especially by the company Engelhard under the names Nu-antique copper 340XB (Cloisonne) and Brown CL4509 (Chromalite); the nacres with a copper glint sold especially by the company Engelhard under the name Copper 340A (Timica); the nacres with a red glint sold especially by the company Merck under the name Sienna fine (17386) (Colorona); the nacres with a yellow glint sold especially by the company Engelhard under the name Yellow (4502) (Chromalite); the red-tinted nacres with a golden glint sold especially by the company Engelhard under the name Sunstone G012 (Gemtone); the pink nacres sold especially by the company Engelhard under the name Tan opale G005 (Gemtone); the black nacres with a golden glint sold especially by the company Engelhard under the name Nu antique bronze 240 AB (Timica); the blue nacres sold especially by the company Merck under the name Matte blue (17433) (Microna); the white nacres with a silvery glint sold especially by the company Merck under the name Xirona Silver; and the golden-green pinkish-orange nacres sold especially by the company Merck under the name Indian summer (Xirona), and mixtures thereof.

When using untreated pigments, the pigment is chosen so as to have a relatively large average particle size, preferably having an average particle size of 0.1 to 50 µm, more preferably 0.1 to 30 µm, and even more preferably 0.1 to 20 µm.

In a particular embodiment, the hydrophilic pigment is an untreated inorganic pigment, preferably an untreated metal oxide, such as titanium oxide and/or iron oxide.

Mentions may be made of, for example, the products sold under the trade name HOMBITAN FF PHARMA from SACHTLEBEN, the products sold under the trade name Sunpuro™ red iron oxide C33-8001 (INCI name iron oxides R), Sunpuro™ black iron oxide C33-7001 (INCI name iron oxides B), or Sunpuro™ yellow iron oxide C33-9001 (INCI name iron oxides Y) by the company SUN.

In another particular embodiment, the hydrophilic pigment is a treated hydrophilic pigment, ie a pigment which has been surface-treated for hydrophilization with any treatment agent which has been conventionally used to confer a hydrophilic property to pigments. Generally, a hydrophilic organic agent for surface-treating a material in order to optimize its dispersion in aqueous medium is more particularly chosen from biological polymers, carbohydrates, polysaccharides, polyacrylates and polyethylene glycol derivatives. The materials thus treated may, in the absence of being soluble in a solvent medium, such as water, be dispersible therein. As examples of biological polymers for coating the dyestuffs to be dissolved according to the invention, mention may be made of polymers based on monomers of carbohydrate type. More particularly, mention may be made of biosaccharide gum, chitosans and derivatives thereof, such as butoxy chitosan, carboxymethyl chitosan, carboxybutyl chitosan, chitosan gluconate, chitosan adipate, chitosan glycolate, chitosan lactate, etc., chitins and derivatives thereof, such as carboxymethyl chitin, chitin glycolate; cellulose and derivatives thereof such as cellulose acetate; microcrystalline cellulose; distarch phosphate; sodium hyaluronate; soluble proteoglycans; galacto-arabinans; glycosaminoglycans; glycogen; sclerotium gum; dextran; starch and derivatives thereof; and mixtures thereof. But it is also possible to use pigments which have been surface-treated by surface treating agents such as in a silica treatment, alumina treatment, silica alumina treatment or a titania treatment.

In the present invention, a silica and silica (and) alumina treatment treatment are especially preferable for selection, and the treatment itself is conventional in the present technical field.

Mentions may be made of such pigments, for example, the products sold under the trade name Sympholight WW (INCI name titanium dioxide and silica and alumina), Sympholight RW-S (INCI name iron oxide and silica), Sympholight BW-S (INCI name iron oxide and silica), Sympholight YW-S (INCI name iron oxide and silica), by the company JGC Catalysts and Chemicals. Advantageously, the composition of the present invention comprises at least one treated hydrophilic pigment chosen from silica and alumina treated titanium dioxide, silica treated iron oxide, or a mixture thereof.

Advantageously, a composition of the invention may comprise at least one hydrophilic pigment in a content ranging from 0.5% to 30% by weight, especially from 1% to 20% and more particularly from 2% to 15% by weight relative to the total weight of the composition.

Fillers

A composition in accordance with the invention may comprise at least one filler of organic or mineral nature.

The term "filler" should be understood to mean colourless or white solid particles of any shape which are in a form that is insoluble and dispersed in the medium of the composition. They are mineral or organic in nature and make it possible to confer softness and mattness on the composition and a uniform makeup result.

The fillers used in the compositions according to the present invention may be in lamellar, globular or spherical form, in the form of fibers or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Among the mineral fillers that can be used in the compositions according to the invention, mention may be made of talc, mica, trimethyl siloxysilicate, kaolin, bentone, calcium carbonate, magnesium hydrogen carbonate, hydroxyapatite, boron nitride, glass or ceramic microcapsules, and mixtures thereof.

A filler suitable for the invention may preferentially be talc, or a mixture thereof.

Among the organic fillers that can be used in the compositions according to the invention, mention may be made of polyamide powders (Nylon® Orgasol from Atochem), poly-β-alanine and polyethylene powders, polytetrafluoroethylene (Teflon® from DuPont) powders, lauroyllysine, starch, modified or unmodified, specially oxidized ester modified starch, such as acetylated oxidized starch sold under the tradename GF-A390 by the company Suzhou Gaofeng, tetrafluoroethylene polymer powders, hollow polymer microspheres, such as Expancel (Nobel Industrie), metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate, Polypore® L 200 (Chemdal Corporation), silicone resin microbeads (Tospearl® from Toshiba, for example), polyurethane powders, in particular powders of crosslinked polyurethane comprising a copolymer, said copolymer comprising trimethylol hexyllactone, for instance the hexamethylene diisocyanate/trimethylol hexyllactone polymer sold under the name Plastic Powder D-400® or Plastic Powder D-800® by the company Toshiki, carnauba microwaxes, such as the product sold under the name MicroCare 350® by the company Micro Powders, microwaxes of synthetic wax, such as the product sold under the name MicroEase 114S® by the company Micro Powders, microwaxes constituted of a mixture of carnauba wax and of polyethylene wax, such as those sold under the names MicroCare 300® and 310® by the company Micro Powders, microwaxes constituted of a mixture of carnauba wax and of synthetic wax, such as the product sold under the name MicroCare 325° by the company Micro Powders, polyethylene microwaxes, such as those sold under the names Micropoly 200®, 220®, 220L® and 250S® by the company Micro Powders; and mixtutres thereof.

Advantageously, the filler suitable for the composition of the present invention is chosen from starch, modified or unmodified, more preferably acetylated oxidized starch.

Preferably, the at least one filler is present in the composition of the present invention from 0 to 20% by weight, preferably from 0.01% to 10%, more preferably from 0.5% to 5% by weight, relative to the total weight of the composition.

Thickeners

The composition according to the invention may comprise at least one thickener chosen from hydrophilic thickeners, lipophilic thickeners, or a mixture thereof.

Hydrophilic Thickeners

The term "hydrophilic thickener" is intended to mean a compound capable of increasing the viscosity of the aqueous phase of the composition.

The hydrophilic thickeners may be used alone or in combination. These thickeners may in particular be chosen from cellulosic polymers and gums.

As hydrophilic thickeners, mention may in particular be made of water-soluble or water-dispersible thickening polymers. They may in particular be chosen from:
  polyvinylpyrrolidone,
  polyvinyl alcohol,
  modified or unmodified carboxyvinyl polymers, such as the products sold under the name Carbopol® (CTFA name: carbomer) by the company Goodrich;
  homopolymers or copolymers of acrylic acid or methacrylic acid or salts thereof and esters thereof, and in particular the products sold under the names Versicol F® or Versicol K® or Salcare SC95 by the company Allied Colloid, Ultrahold 8® by the company Ciba-Geigy, polyacrylates and polymethacrylates, such as the products sold under the names Lubrajel and Norgel by the company Guardian or under the name Hispagel by the company Hispano Chimica, polyacrylic acids of Synthalen K type;
  polyacrylamides;
  copolymers of acrylic acid and of acrylamide sold in the form of their sodium salt under the names Reten® by the company Hercules, poly(sodium methacrylate) sold under the name Darvan No7® by the company Vanderbilt, the sodium salts of polyhydroxycarboxylic acids sold under the name Hydagen F® by the company Henkel;
  2-acrylamido-2-methylpropanesulfonic acid polymers and copolymers, which are optionally crosslinked and/or neutralized, for instance the poly(2-acrylamido-2-methylpropanesulfonic acid) sold by the company Clariant under the name Hostacerin AMPS (CTFA name: ammonium polyacryldimethyltauramide);
  crosslinked anionic acrylamide/AMPS copolymers, in the form of a W/O emulsion, such as those sold under the name Sepigel 305 (CTFA name: Polyacrylamide/C13-14 Isoparaffin/Laureth-7) and under the name Simulgel 600 (CTFA name: Acrylamide/Sodium acryloyldimethyltaurate copolymer/Isohexadecane/Polysorbate 80) by the company SEPPIC;
  polyacrylic acid/alkyl acrylate copolymers of Pemulen type;
  polysaccharide biopolymers, for instance xanthan gum, guar gum, gum Arabic, locus bean gum, acacia gum, scleroglucans, chitin derivatives and chitosan derivatives, carrageenans, gellans, alginates, or celluloses such as microcrystalline cellulose, carboxymethylcellulose, hydroxymethylcellulose, hydroxyethylcellulose and hydroxypropylcellulose. Mentions maybe made of, for example, xanthan gum sold under the trade name Keltrol® CG-T by the company CP Kelco;
  hydrophilic fumed silicas obtained by high-temperature hydrolysis of a volatile silicon compound in an oxyhydrogen flame, producing a finely divided silica. The hydrophilic silicas have a large number of silanol groups at their surface. Such hydrophilic silicas are, for example, sold under the names Aerosil 130®, Aerosil 200®, Aerosil 255®, Aerosil 300® and Aerosil 380® by the company Degussa, or Cab-O-Sil Cab-O-Sil EH-5®, Cab-O-Sil LM-130®, Cab-O-Sil MS-55® and Cab-O-Sil M-5® by the company Cabot. They preferably have a particle size that can be nanometric to micrometric, for example ranging from about 5 to 200 nm;
  hydrophilic clays;
  associative polymers, for instance the PEG-150/stearyl alcohol/SMDI copolymer sold under the name Aculyn 46 by Rohm & Haas, or the steareth-100/PEG-136/HDI copolymer sold under the name Rheolate FX 1100 by Elementis;
  and mixtures thereof.

Lipophilic Thickeners

The term "lipophilic thickener" is intended to mean a compound capable of increasing the viscosity of the fatty phase of the composition.

Preferably the lipophilic thickener is chosen from mineral lipophilic thickeners.

Mention may in particular be made of lipophilic clays, for instance optionally modified clays, such as hectorites modified with a $C_{10}$ to $C_{22}$ ammonium chloride, for instance hectorite modified with distearyldimethylammonium chloride.

Clays are silicates containing a cation which can be chosen from calcium, magnesium, aluminum, sodium, potassium and lithium cations, and mixtures thereof.

By way of examples of such products, mention may be made of clays of the smectite family, such as montmorillonites, hectorites, bentonites, beidellites or saponites, and also of the vermiculite, stevensite and chlorite family. These clays may be of natural or synthetic origin.

The clay may be chosen from montmorrillonite, bentonite, hectorite, attapulgite and sepiolite, and mixtures thereof. The clay is preferably a bentonite or a hectorite.

Organophilic clays are clays modified with a chemical compound chosen from quaternary amines, tertiary amines, amine acetates, imidazolines, amine soaps, fatty sulfates, alkyl aryl sulfonates and amine oxides, and mixtures thereof.

As organophilic clays, mention may be made of quaternium-18 bentonites such as those sold under the names Bentone 3, Bentone 38 and Bentone 38V by the company Elementis, Tixogel VP by the company United Catalyst, Claytone 34, Claytone 40 and Claytone XL by the company Southern Clay; stearalkonium bentonites such as those sold under the names Bentone 27V by the company Elementis, Tixogel LG by the company United Catalyst, and Claytone AF and Claytone APA by the company Southern Clay; quaternium-18/benzalkonium bentonites such as those sold under the names Claytone HT and Claytone PS by the company Southern Clay, disteardimonium hectorite such as those sold under the name Bentone 38 VCG by the company ELEMENTIS, and a mixture thereof.

According to one preferred embodiment, the lipophilic thickener is chosen from organophilic modified clays, such as disteardimonium hectorite.

Mention may also be made of hydrophobic silicas, for instance fumed silica optionally subjected to a hydrophobic surface treatment, the particle size of which is less than 1 μm. It is in fact possible to chemically modify the surface of the silica, by chemical reaction generating a reduced number of silanol groups present at the surface of the silica. It is in particular possible to substitute silanol groups with hydrophobic groups: a hydrophobic silica is then obtained. The hydrophobic groups may be:

trimethylsiloxyl groups, which are in particular obtained by treatment of fumed silica in the presence of hexamethyldisilazane. Silicas thus treated are known as "silica silylate" according to the CTFA (6th edition, 1995). They are sold, for example, under the references Aerosil R812® by the company Degussa, and Cab-O-Sil TS-530® by the company Cabot;

dimethylsilyloxyl or polydimethylsiloxane groups, which are obtained in particular by a treatment of fumed silica in the presence of polydimethylsiloxane or of dimethyldichlorosilane. Silicas thus treated are known as "silica dimethyl silylate" according to the CTFA (6th edition, 1995). They are, for example, sold under the references Aerosil R972® and Aerosil R974® by the company Degussa, and Cab-O-Sil TS-610® and Cab-O-Sil TS-720® by the company Cabot.

The hydrophobic fumed silica preferably has a particle size that may be nanometric to micrometric, for example ranging from about 5 to 200 nm.

According to a preferred embodiment, the thickener, if present is chosen from xanthan gum, disteardimonium hectorite, silica silylate, or a mixture thereof, more preferably, the thickener is disteardimonium hectorite.

The at least one thickener may be present in the composition according to the invention from 0 to 20% by weight, preferably in a content ranging from 0.01% to 10% by weight and preferentially ranging from 0.5% to 5% by weight relative to the total weight of the composition.

Galenic Form

The composition according to the invention may be in various forms, in particular in the form of dispersion or emulsion, especially such as a water/oil or oil/water emulsion or multiple emulsions.

Dispersion may be made as an aqueous phase or as an oily phase.

An emulsion may have an oily or aqueous continuous phase. Such an emulsion may be, for example, an inverse (W/O) emulsion or a direct (O/W) emulsion, or alternatively a multiple emulsion (W/O/W or O/W/O).

In the case of emulsions, a multiple emulsion, especially oil-in-water-in-oil emulsion is preferred.

According to a preferred embodiment of the present invention, the composition is prepared following the steps of:

1) adding at least one third surfactant and at least one hydrophilic pigment as defined in the present invention to water, mixing until homogeneous under room temperature (25° C.), obtaining a phase B;

2) mixing at least one oil with the phase B, mixing for 15 minutes by stirring to obtain emulsion 1, which is a oil-in-water emulsion;

3) mixing at least one first surfactant chosen from $C_8$-$C_{22}$ alkyl dimethicone copolyols and at least one second surfactant chosen from dimethicone copolyols, which is different from the first surfactant, and/or at least one oil to obtain a fatty phase A;

4) adding the emulsion 1 obtained in step 2) to the fatty phase A obtained in step 3), homogenizing the mixture by stirring, to form a oil-in-water-in-oil emulsion.

Additives

In a particular embodiment, a cosmetic composition according to the invention further comprises at least one compound chosen from hydrophilic solvents, lipophilic solvents, additional oils, and mixtures thereof.

A cosmetic composition according to the invention may also comprise any additive usually used in the field under consideration, chosen, for example, from gums, resins, additional thickening agents, structuring agents such as waxes, dispersants, antioxidants, essential oils, preserving agents, fragrances, neutralizers, antiseptics, additional UV-screening agents, cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the invention such that the desired cosmetic properties and stability properties thereof are not thereby affected.

Method and Use

The composition of the present invention can be used for a non-therapeutic process, such as a process for caring for/making up the skin, in particular the face, comprising the application to the skin of the composition according to the present invention.

The present invention also relates to a use of the composition according to the present invention, as it is or in cosmetic product for making up/caring for/cleansing/make up removing products for the skin, especially for the face and the lips.

The examples that follow are aimed at illustrating the compositions and processes according to this invention, but are not in any way a limitation of the scope of the invention. All the parts and percentages in the examples are given on a weight basis and all the measurements were obtained at about 25° C., unless otherwise mentioned.

EXAMPLES

Example 1: Formulation Example

The following compositions were prepared (inv comp stands for invention compositions, compa comp stands for comparative compositions):

| Phase | INCI name | % of ingredient by raw material (wt %) | | | | |
|---|---|---|---|---|---|---|
| | | Inv comp 1 | Inv comp 2 | Compa comp 1 | Compa comp 2 | Compa comp 3 |
| Fatty phase-A1 | CETYL PEG/PPG-10/1 DIMETHICONE (ABIL ® EM 90 from EVONIK GOLDSCHMIDT) | 3 | 3 | 3 | 3 | 3 |
| | PEG-10 DIMETHICONE (KF-6017 from SHIN ETSU) | 2 | 2 | 2 | 2 | 2 |
| Third surfactants | POLYGLYCERYL-4 CAPRATE (TEGOSOFT ® PC 41 from EVONIK GOLDSCHMIDT) | 5.3 | 0 | 5.3 | 0 | 0 |
| | GLYCERYL STEARATE (and) PEG-100 STEARATE (SIMULSOL ™ 165 from SEPPIC) | 0 | 2 | 0 | 0 | 0 |
| | DECYL GLUCOSIDE (PLANTACARE ® 2000 UP from COGNIS (BASF)) | 0 | 3 | 0 | 0 | 0 |
| | POLYGLYCERYL ISOSTEARATE (ISOLAN ® GI 34 from EVONIC GOLDSCHMIDT) with HLB less than 8 | 0 | 0 | 0 | 0 | 5.3 |
| Pigments | TITANIUM DIOXIDE (and) SILICA (and) ALUMINA (SYMPHOLIGHT WW from JGC CATALYSTS AND CHEMICALS) | 8.7 | 0 | 0 | 8.7 | 8.7 |
| | IRON OXIDES (and) SILICA (SYMPHOLIGHT RW-S from JGC CATALYSTS AND CHEMICALS) | 0.3 | 0 | 0 | 0.3 | 0.3 |
| | IRON OXIDES (and) SILICA (SYMPHOLIGHT BW-S from JGC CATALYSTS AND CHEMICALS) | 0.14 | 0 | 0 | 0.14 | 0.14 |
| | IRON OXIDES (and) SILICA (SYMPHOLIGHT YW-S from JGC CATALYSTS AND CHEMICALS) | 0.86 | 0 | 0 | 0.86 | 0.86 |
| | TITANIUM DIOXIDE (HOMBITAN FF PHARMA from SACHTLEBEN) | 0 | 8.65 | 0 | 0 | 0 |
| | IRON OXIDES R (SUNPURO ™ RED IRON OXIDE C33-8001 from SUN) | 0 | 0.3 | 0 | 0 | 0 |
| | IRON OXIDES R (SUNPURO ™ BLACK IRON OXIDE C33-7001 from SUN) | 0 | 0.15 | 0 | 0 | 0 |
| | IRON OXIDES R (SUNPURO ™ YELLOW IRON OXIDE C33-9001 from SUN) | 0 | 0.9 | 0 | 0 | 0 |
| | IRON OXIDES COATED WITH PERFLUOROALKYL | 0 | 0 | 0.9 | 0 | 0 |

|  |  | % of ingredient by raw material (wt %) | | | | |
|---|---|---|---|---|---|---|
| Phase | INCI name | Inv comp 1 | Inv comp 2 | Compa comp 1 | Compa comp 2 | Compa comp 3 |
|  | PHOPHATE (FA50DYF from KOBO) |  |  |  |  |  |
|  | IRON OXIDES COATED WITH PERFLUOROALKYL PHOPHATE (FA50DRF from KOBO) | 0 | 0 | 0.3 | 0 | 0 |
|  | IRON OXIDES COATED WITH PERFLUOROALKYL PHOPHATE (FA65DBF from KOBO) | 0 | 0 | 0.15 | 0 | 0 |
|  | TITANIUM OXIDES COATED WITH PERFLUOROALKYL PHOPHATE (FA65DF from KOBO) | 0 | 0 | 8.65 | 0 | 0 |
| Thickeners | DISTEARDIMONIUM HECTORITE (BENTONE® 38 VCG from ELEMENTIS) | 0 | 1 | 0 | 0 | 0 |
| Fillers | ACETYLATED OXIDATED STARCH (GF-A390 from SUZHOU GAOFENG STARCH TECHNOLOGY) | 0 | 1 | 0 | 0 | 0 |
| Fatty phase A1 | CYCLOHEXASILOXANE (XIAMETER® PMX-0246 CYCLOHEXASILOXANE (DOW CORNING)) | 18.5 | 16.5 | 18.5 | 18.5 | 18.5 |
| Fatty phase A2 | SQUALANE (PRIPURE 3759-LQ-(GD) (CRODA)) | 5 | 5 | 5 | 0 | 5 |
| Aqueous phase | Water | Qs 100 | Qs 100 | Qs 100 | Qs 100 | Qs 100 |

Remarks:

Invention composition 1 comprises hydrophilic treated pigments;

Invention composition 2 comprises hydrophilic untreated pigments;

Comparative composition 1 comprises hydrophobic treated pigments;

Comparative composition 2 does not comprise the said third surfactant;

Comparative composition 3 comprises polyglyceryl isostearate with HLB value less than 8.

The compositions as listed above were prepared following the steps of:

1) adding the third surfactants and pigments to the aqueous phase, mixing the mixture until homogeneous under room temperature (25® C.), obtaining a phase B;

2) adding fatty phase A2 to the phase B, homogenizing for 15 minutes by stirring to obtain emulsion 1, which is a O2/W emulsion;

3) adding the thickener, if any, to the fatty phase A1, mixing the mixture until homogeneous, obtaining fatty phase A;

4) adding the emulsion 1 obtained in step 2) to the fatty phase A obtained in step 3), homogenizing the mixture by stirring.

Example 2: Evaluation Example

Evaluations of the makeup effect such as homogeneity and long lasting, and water washability effect of the invention compositions 1 and 2 and comparative compositions 1, 2, and 3 prepared above were performed, by means of Chromasphere with a definition of 410×410 pixels, according to the following protocol:

the measurements were taken in a standardized manner at 20° C., before and after application with the bare fingers (for makeup effect evaluation), or washing with lukewarm water after application (for water washability effect evaluation), of the composition onto the skin of a model.

Evaluations of the above mentioned effects of the compositions were also performed by the panelists.

Protocol for instrumental measurements of the makeup effect and water washability effect A colorimetric measurement of the skin before and after making up was carried out by measuring the means for the planes of 10 women models, C* (chroma, the distance out from the neutral axis-saturationv), H* (hue, the angle/direction in the 360 degree range), and L* (lightness), respectively. For each of the 10 women models, an image was taken using a Chromasphere with a definition of 410×410 pixels. The results were expressed in the following manner: the color was quantified by the C* (chroma, the distance out from the neutral axis-saturationv), H* (hue, the angle/direction in the 360 degree range), and L* (lightness) analysed by the camera. The homogeneity and long lasting were calculated by the variation of these variables after 3 hours of makeup (deltaE$_{94}$). The deltaE, dE or else $\Delta E_{94}$ is defined as a measurement of difference between two colors. The formula was published in 1995 by a technical committee of the CIE (TC 1-29), as shown below:

$$\Delta E_{94}^* = \sqrt{\left(\frac{\Delta L^*}{K_L}\right)^2 + \left(\frac{\Delta C_{ab}^*}{1+K_1 C_1^*}\right)^2 + \left(\frac{\Delta H_{ab}^*}{1+K_2 C_1^*}\right)^2}$$

where in:

$$\Delta L^* = L_1^* - L_2^*$$

$$\Delta C_{ab}^* = C_1^* - C_2^*$$

$$\Delta H_{ab}^* = \sqrt{\Delta E_{ab}^{*2} - \Delta L^{*2} - \Delta C_{ab}^{*2}}$$

$K_L$, $K_1$ and $K_2$ are weighting factors;
$L_1^*$, $C_1^*$ and $H_1^*$ are the coordinates in the colorimetric space of the first color to be compared and $L_2^*$, $C_2^*$ and $H_2^*$ those of the second.

More specifically, the measurements of makeup effect (homogeneity and long lasting) were carried out and the measurements were made at the following times:

$T_0$=measurement on naked skin freed of makeup, before application of the test composition $T_{imm}$=measurement after application and drying (10 minutes) of the test composition $T_{3h}$=measurement 3 hours after application of the composition $(T_{imm}-T_O)$ measurement of the homogeneity of the composition $(T_{3h}-T_{imm})$ measurement of the long lasting of the composition The measurements were performed on a panel of 10 women models who were kept in an air-conditioned (22° C.+/−2° C.) waiting room for 15 min before the beginning of the test. They removed their makeup and an image of one of their cheeks was acquired using the Chromasphere with a definition of 410×410 pixels. This image made it possible to measure the color at $T_0$ before applying makeup. Approximately 100 mg of the invention compositions 1 and 2, and the comparative compositions 1, 2, and 3 formulated in the formulation example were then weighed out into a watch glass and were applied with the bare fingers, respectively, to the half of the face on which the measurement was carried out at $T_0$.

Right after application of the compositions, an image of the made-up cheek was acquired using the Chromasphere. This image made it possible to measure the color immediately after applying the compositions $(T_{imm})$. The women models then returned to the air-conditioned room for 3 hours. Finally, an image of the made-up cheek after waiting for 3 hours was acquired using the Chromasphere. This image made it possible to measure the color after wearing the compositions for 3 h $(T_{3h})$.

Each image obtained using the camera was processed by coxellography. The standard deviation of each monochrome plane was calculated. The product of the three standard deviations was equal to the coxellographic index. This parameter was used for the statistical calculation. The more uniform the skin, the smaller the standard deviation. The coxellographic index changes in the same way since it is the product of the standard deviations of the three planes C* (chroma), H* (hue), and L* (lightness).

The results were expressed by calculating the difference $(T_{imm}-T_0)$, which measures the homogeneity, and the difference $(T_{3h}-T_{imm})$ measures the long lasting.

For the measurements performed, it was considered that:
+poor homogeneity or no long lasting effect;
++good homogeneity or good long lasting
+++very strong homogeneity or very good long lasting The measurements of water washability effect were carried out and the measurements were made at the following times:

$T_{10min}$=measurement 10 minutes after application of the composition $T_{20min}$=measurement 20 minutes after washing the skin where the composition is applied on by the lukewarm water $(T_{10min}-T_0)$ and $(T_{20min}-T_0)$ measurement of the water washability of the composition The measurements were performed on a panel of 10 women models who were kept in an air-conditioned (22° C.+/−2° C.) waiting room for 15 min before the beginning of the test. They removed their makeup and an image of one of their cheeks was acquired using the Chromasphere with a definition of 410×410 pixels. This image made it possible to measure the color at $T_0$ before applying makeup. Approximately 10 mg of the invention compositions 1 and 2, and the comparative compositions 1, 2, and 3 were then weighed out into a watch glass and were applied with the bare fingers, respectively, to the face skin of a 12.56 cm² area on which the $T_0$ measurement was carried out.

After a drying time of 10 min, an image of the made-up cheek area was acquired using the Chromasphere. This image made it possible to measure the color immediately after applying makeup $(T_{10min})$. Then the made-up cheek was washed by lukewarm water. Finally, an image of the cleaned cheek area after waiting for 20 minutes after washing of the made-up cheek area was acquired using the Chromasphere. This image made it possible to measure the color after washing of the made-up cheek area $(T_{20min})$.

The results were expressed by the following equation:

Difference (%)={[$\Delta E_{94}(T_{10min}-T_0)-\Delta E_{94}(T_{20min}-T_0)$]/$\Delta E_{94}(T_{10min}-T_0)$}×100%

The higher the difference (%) is, the better the water washability of the composition. The products exhibit excellent water washability if the difference is greater than 80%, preferably greater than 85%. The products do not possess an acceptable water washability effect if the difference is lower than 70%.

Protocol for panel evaluations of the makeup effect and water washability effect of the compositions Finally, the scores of the makeup effects and the water washability effects of the invention compositions 1 and 2, and the comparative compositions 1 to 3 were given by the panelists of the 10 women models, respectively.

Makeup effects were evaluated by the panelists 15 minutes after 100 mg of the compositions prepared in formulation example on half of the face of the women models, respectively.

Water washability effects were evaluated by the same panelists 20 minutes after washing the half face where the compositions were applied on by lukewarm water.

5: very good
4: basically good;
3: acceptable;
2: slightly poor and not acceptable;
1: poor, not acceptable.

The result of the makeup effects and water washability effects were as follow:

| Test | Inv comp 1 | Inv comp 2 | Compa comp 1 | Compa comp 2 | Compa comp 3 |
|---|---|---|---|---|---|
| Homogeneity (Coxelo ($T_{imm}$ – $T_0$)) | +++ | +++ | +++ | +++ | +++ |
| Long lasting (eveness) (Coxelo ($T_{3h}$ – $T_{imm}$)) | +++ | +++ | +++ | +++ | +++ |
| Long lasting (color) ($\Delta E_{94}$ ($T_{3h}$ – $T_{imm}$)) | 0.891 | 0.93 | 1.026 | 0.91 | 0.90 |
| Water washability (Difference %) | 88.36% | 89.79% | 46.35% | 68.84% | 37.42% |
| Makeup effect evaluated by the panelists | 5 | 5 | 5 | 5 | 4 |
| Washability effect evaluated by the panelists | 5 | 5 | 1 | 2 | 1 |

From the results listed above, it is observed that the invention compositions 1 and 2, comparing to the comparative inventions 1, 2, and 3, possess good makeup effect, while only the invention compositions 1 and 2 exhibit optimized water washability effect, comparing to the comparative compositions 1, 2, and 3.

Based on the above listed evaluation results, the inventors discovered that the composition according to the present invention overcomes the technical issues existing in the prior art, and provides a stable cosmetic composition with optimized water washability effect, and meanwhile maintaining good make up effect.

What is claimed is:

1. A cosmetic composition comprising at least one fatty phase, aqueous phase, and relative to the total weight of the composition:
    a) from 1% to 5% by weight of cetyl PEG/PPG-10/1 dimethicone as a first surfactant;
    b) from 0.8% to 3% by weight of PEG-10 dimethicone as a second surfactant;
    c) from 1% to 5% by weight of a third surfactant which is a mixture of glycerol stearate, PEG-100 stearate and decyl glucoside;
    d) from 2% to 15% by weight of a pigment selected from the group consisting of iron oxide and titanium dioxide;
    e) from 0.5% to 5% by weight of an organic filler or a mineral filler; and
    f) from 0.5% to 5% by weight of an organophilic clay thickener;

wherein
    the fatty phase is from 5% to 35% by weight relative to the total weight of the composition, and
    the composition is in the form of an oil-in-water-in-oil emulsion.

* * * * *